(12) United States Patent
Spirer (10) Patent No.: US 11,756,679 B2
(45) Date of Patent: Sep. 12, 2023

(54) TASK MANAGEMENT SYSTEM

(71) Applicant: Dilogr, LLC, Austin, TX (US)

(72) Inventor: Gary Spirer, Austin, TX (US)

(73) Assignee: Dilogr, LLC, Austin, TX (US)

( * ) Notice: Subject to any disclaimer, the term of this patent is extended or adjusted under 35 U.S.C. 154(b) by 972 days.

(21) Appl. No.: 16/408,344

(22) Filed: May 9, 2019

(65) Prior Publication Data

US 2019/0348174 A1 Nov. 14, 2019

Related U.S. Application Data

(60) Provisional application No. 62/668,884, filed on May 9, 2018.

(51) Int. Cl.
| | | |
|---|---|---|
| *G16H 40/40* | (2018.01) | |
| *G06Q 10/0631* | (2023.01) | |
| *G06Q 30/018* | (2023.01) | |
| *G06F 40/205* | (2020.01) | |

(52) U.S. Cl.
CPC .......... *G16H 40/40* (2018.01); *G06F 40/205* (2020.01); *G06Q 10/063114* (2013.01); *G06Q 30/018* (2013.01)

(58) Field of Classification Search
CPC ..... G16H 40/40; G06F 40/205; G06Q 30/018
See application file for complete search history.

(56) References Cited

U.S. PATENT DOCUMENTS

| | | | |
|---|---|---|---|
| 8,381,305 B2 * | 2/2013 | Jacobson | H04L 63/20 726/1 |
| 8,738,492 B1 | 5/2014 | Stuart | |
| 8,887,047 B2 * | 11/2014 | DiGiantomasso | G09B 5/00 434/350 |
| 10,891,956 B2 * | 1/2021 | Canim | G10L 15/22 |
| 2002/0023109 A1 | 2/2002 | Lederer, Jr. et al. | |
| 2002/0143595 A1 | 10/2002 | Frank et al. | |
| 2004/0073868 A1 | 4/2004 | Easter et al. | |
| 2017/0116881 A1 * | 4/2017 | Cohen | G09B 5/10 |

OTHER PUBLICATIONS

How to send an email message with reminder in Outlook?, https://web.archive.org/web/20140818075613/https://www.extendoffice.com/documents/outlook/1785-outlook-send-email-with-reminder.html (Year: 2014).*

(Continued)

*Primary Examiner* — Aryan E Weisenfeld
(74) *Attorney, Agent, or Firm* — Kunzler Bean & Adamson (57) ABSTRACT

Apparatuses, methods, systems, and program products are disclosed for task management. An apparatus includes a processor and a memory that stores code executable by the processor. The executable code includes code to receive information for defining one or more form fields of a compliance template associated with a compliance task. The information is derived from a compliance policy. The executable code includes code to include one or more interactive multimedia elements in the compliance template. The one or more interactive multimedia elements are associated with at least one of the one or more form fields. The executable code includes code to electronically present the compliance template during the compliance task to gather compliance information related to the compliance task.

20 Claims, 5 Drawing Sheets

(56) References Cited

OTHER PUBLICATIONS

PCT/US2019/031619, "Notification of Transmittal of the International Search Report and the Written Opinion of the International Searching Authority, or the Declaration", PCT International Searching Authority, dated Jul. 29, 2019, pp. 1-9.

Qing Hu et al., "Managing Employee Compliance with Information Security Policies: The Critical Role of Top Management and Organizational Culture", Decision Sciences, vol. 43 No. 4, Aug. 2012, pp. 615-659.

* cited by examiner

TASK MANAGEMENT SYSTEM

CROSS-REFERENCES TO RELATED APPLICATIONS

This application claims the benefit of U.S. Provisional Patent Application No. 62/668,884 entitled "TASK MANAGEMENT SYSTEM" and filed on May 9, 2018, for Gary Spirer, which is incorporated herein by reference.

FIELD

This invention relates to task management and more particularly relates to task management for compliance tasks.

BACKGROUND

Compliance management is crucial for certain organizations that rely on accreditation to continue to operate. However, keeping track of compliance tasks and when the compliance tasks need to be completed can be an overwhelming and painstaking task.

BRIEF SUMMARY

Apparatuses, methods, systems, and program products are disclosed for task management. In one embodiment, an apparatus includes a processor and a memory that stores code executable by the processor. The executable code includes code to receive information for defining one or more form fields of a compliance template associated with a compliance task. The information is derived from a compliance policy. The executable code includes code to include one or more interactive multimedia elements in the compliance template. The one or more interactive multimedia elements are associated with at least one of the one or more form fields. The executable code includes code to electronically present the compliance template during the compliance task to gather compliance information related to the compliance task.

A method for task management, in one embodiment, includes receiving information for defining one or more form fields of a compliance template associated with a compliance task. The information is derived from a compliance policy. A method, in certain embodiments, further includes including one or more interactive multimedia elements in the compliance template. The one or more interactive multimedia elements are associated with at least one of the one or more form fields. In some embodiments, the method includes electronically presenting the compliance template during the compliance task to gather compliance information related to the compliance task.

A computer program product includes a computer readable storage medium that stores code executable by a processor. In one embodiment, the executable code includes code to perform receiving information for defining one or more form fields of a compliance template associated with a compliance task. The information is derived from a compliance policy. In some embodiments, the executable code includes code to perform including one or more interactive multimedia elements in the compliance template. The one or more interactive multimedia elements are associated with at least one of the one or more form fields. In further embodiments, the executable code includes code to perform electronically presenting the compliance template during the compliance task to gather compliance information related to the compliance task.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory ("RAM"), a read-only memory ("ROM"), an erasable programmable read-only memory ("EPROM" or Flash memory), a static random access memory ("SRAM"), a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program instructions may, for instance, comprise one or more physical or logical blocks of computer instructions which may, for instance, be organized as an object, procedure, or function. Nevertheless, the executables of an identified module need not be physically located together but may comprise disparate instructions stored in different locations which, when joined logically together, comprise the module and achieve the stated purpose for the module.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Apparatuses, methods, systems, and program products are disclosed for task management. In one embodiment, an apparatus includes a processor and a memory that stores code executable by the processor. The executable code includes code to receive information for defining one or more form fields of a compliance template associated with a compliance task. The information is derived from a compliance policy. The executable code includes code to include one or more interactive multimedia elements in the compliance template. The one or more interactive multimedia elements are associated with at least one of the one or more form fields. The executable code includes code to electronically present the compliance template during the compliance task to gather compliance information related to the compliance task.

In one embodiment, the code is further executable by the processor to assign the compliance template to a building of an organization. The template may include one of a plurality of templates assigned to the building and associated with different compliance tasks for the building. In some embodiments, the code is further executable by the processor to parse the compliance policy using natural language processing to identify different compliance tasks and requirements for completing a compliance task and automatically generate the information that defines the one or more form fields for the compliance template based on the identified requirements for the compliance tasks.

In one embodiment, the one or more interactive multimedia elements is selected from the group consisting of a survey, a quiz, an instructional video, a training video, a webinar, and a how-to slideshow. In certain embodiments, the code is further executable by the processor to assign one or more users to the compliance task associated with the compliance template such that the one or more users are the only users allowed to enter compliance information into the compliance template to complete the compliance task.

In various embodiments, the code is further executable by the processor to provide the compliance information that is entered into the compliance template to an accreditation service as evidence of an organization's compliance with the compliance policy. In further embodiments, the compliance template includes a deadline for completing the compliance task associated with the compliance template. The deadline may be defined by the compliance policy.

In one embodiment, the code is further executable by the processor to generate a compliance schedule for the compliance task based on the deadline for completing the compliance task. In certain embodiments, the code is further executable by the processor to generate one or more reminders for completing the compliance task at predefined points in time prior to the deadline. In one embodiment, the code is further executable by the processor to send the one or more reminders to one or more users who are assigned to the compliance task at the predefined points in time prior to the deadline in response to the compliance task not being completed.

In certain embodiments, the code is further configured to generate one or more work orders for one or more third-party vendors based on the compliance task and a schedule for completion of the compliance task. In one embodiment, the one or more work orders are for third-party services selected from the group comprising maintenance services, inspection services, and equipment management services.

In one embodiment, the compliance task is associated with one or more pieces of equipment. The one or more pieces of equipment may be identified using an identification tag located on the one or more pieces of equipment and a location service that is configured to determine the location of the one or more pieces of equipment based on the identification tag. In some embodiments, the compliance policy and the compliance task are associated with a healthcare organization.

A method for task management, in one embodiment, includes receiving information for defining one or more form fields of a compliance template associated with a compliance task. The information is derived from a compliance policy. A method, in certain embodiments, further includes including one or more interactive multimedia elements in the compliance template. The one or more interactive multimedia elements are associated with at least one of the one or more form fields. In some embodiments, the method includes electronically presenting the compliance template during the compliance task to gather compliance information related to the compliance task.

In one embodiment, the method includes assigning the compliance template to a building of an organization, the template comprising one of a plurality of templates assigned to the building and associated with different compliance tasks for the building. In some embodiments, the method includes assigning one or more users to the compliance task associated with the compliance template such that the one or more users are the only users allowed to enter compliance information into the compliance template to complete the compliance task.

In certain embodiments, the compliance template includes a deadline for completing the compliance task associated with the compliance template. The deadline may be defined by the compliance policy. In one embodiment, the method includes generating a compliance schedule for the compliance task based on the deadline for completing the compliance task, generating one or more reminders for completing the compliance task at predefined points in time prior to the deadline, and sending the one or more reminders to one or more users who are assigned to the compliance task at the predefined points in time prior to the deadline in response to the compliance task not being completed.

A computer program product includes a computer readable storage medium that stores code executable by a processor. In one embodiment, the executable code includes code to perform receiving information for defining one or more form fields of a compliance template associated with a compliance task. The information is derived from a compliance policy. In some embodiments, the executable code includes code to perform including one or more interactive multimedia elements in the compliance template. The one or more interactive multimedia elements are associated with at least one of the one or more form fields. In further embodiments, the executable code includes code to perform electronically presenting the compliance template during the compliance task to gather compliance information related to the compliance task.

Figure 1:
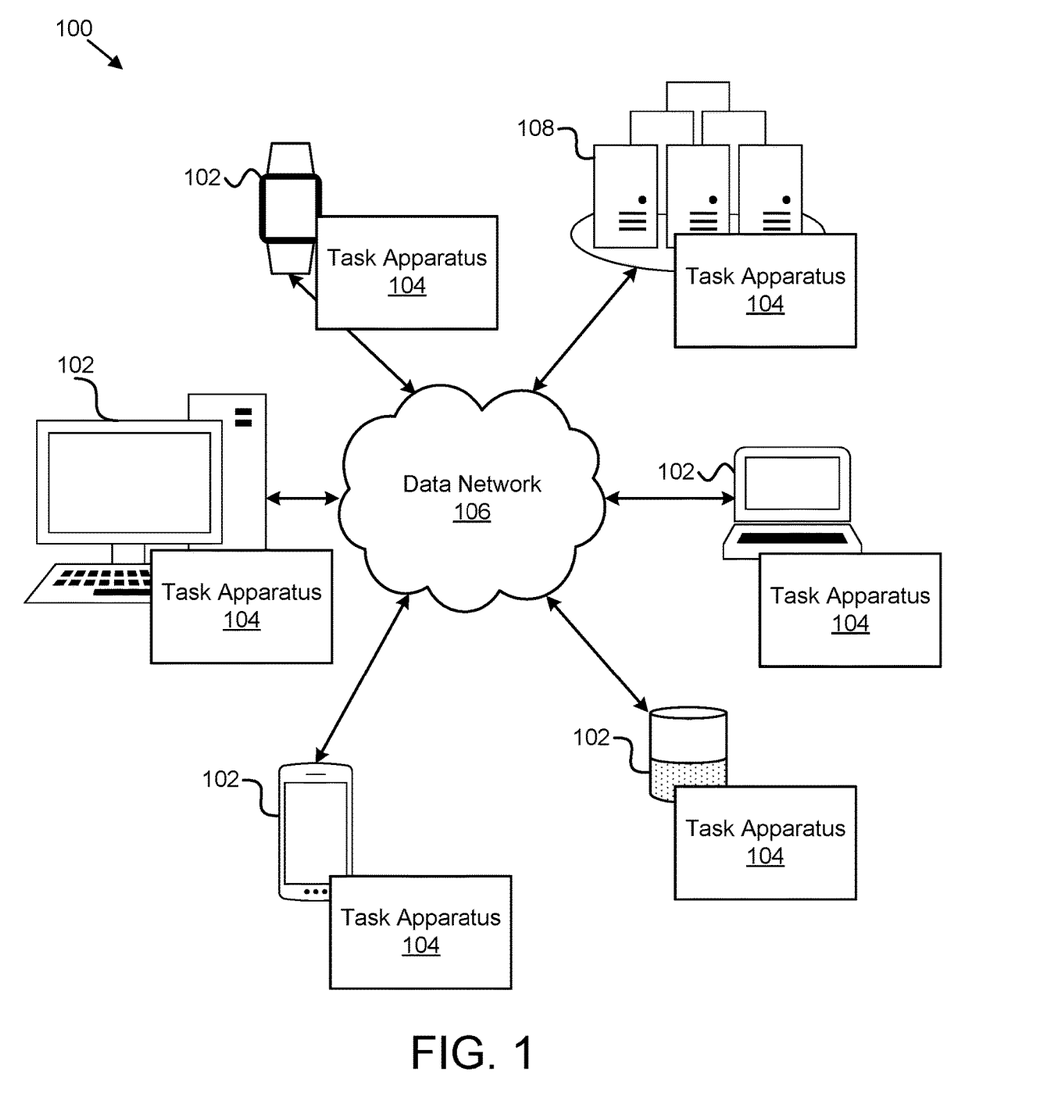
FIG. 1 is a schematic block diagram illustrating one embodiment of a system for task management.

FIG. 1 is a schematic block diagram illustrating one embodiment of a task management system 100. In one embodiment, the system 100 includes one or more information handling devices 102, one or more task apparatuses 104, one or more data networks 106, and one or more servers 108. In certain embodiments, even though a specific number of information handling devices 102, task apparatuses 104, data networks 106, and servers 108 are depicted in FIG. 1, one of skill in the art will recognize, in light of this disclosure, that any number of information handling devices 102, task apparatuses 104, data networks 106, and servers 108 may be included in the system 100.

In one embodiment, the system 100 includes one or more information handling devices 102. The information handling devices 102 may include one or more of a desktop computer, a laptop computer, a tablet computer, a smart phone, a smart speaker (e.g., Amazon Echo®, Google Home®, Apple HomePod®), a security system, a set-top box, a gaming console, a smart TV, a smart watch, a fitness band or other wearable activity tracking device, an optical head-mounted display (e.g., a virtual reality headset, smart glasses, or the like), a High-Definition Multimedia Interface ("HDMI") or other electronic display dongle, a personal digital assistant, a digital camera, a video camera, or another computing device comprising a processor (e.g., a central processing unit ("CPU"), a processor core, a field programmable gate array ("FPGA") or other programmable logic, an application specific integrated circuit ("ASIC"), a controller, a microcontroller, and/or another semiconductor integrated circuit device), a volatile memory, and/or a non-volatile storage medium.

In certain embodiments, the information handling devices 102 are communicatively coupled to one or more other information handling devices 102 and/or to one or more servers 108 over a data network 106, described below. The information handling devices 102, in a further embodiment, may include processors, processor cores, and/or the like that are configured to execute various programs, program code, applications, instructions, functions, and/or the like. The information handling devices 102 may include executable code, functions, instructions, operating systems, and/or the like for task management.

In one embodiment, the task apparatus 104 is configured to create one or more compliance templates based on a compliance policy, manual, or the like. As used herein, compliance refers to adherence to a predefined set of standards, regulations, rules, and/or other requirements as established by a board or organization (e.g., an accreditation organization, a government agency, or the like). The compliance templates are associated with various compliance tasks and allow the user to enter information into the template during the compliance task. For example, the compliance task may be to check the status of fire extinguishers on a floor of a hospital. A template may be created for a particular fire extinguisher on the floor that allows a user to enter information about the fire extinguisher such as the current date, the expiration date of the fire extinguisher, whether the fire extinguisher is full, and/or the like. The template may allow the user to upload images or videos of the fire extinguisher during the compliance check.

The template may also include interactive multimedia video, images, slideshows, or the like that may show the user how to check the fire extinguisher, may help the user locate the fire extinguisher, or the like. The interactive multimedia content may include survey questions, for example, such as "did you check the expiration date?", "did you remember to check the level of the fire extinguisher?", "are there any objects obstructing the path to the fire extinguisher?", and/or the like. A video, for example, may pause and resume playing at a position in the video based on the answer to the questions. For instance, if the user asserts that he did not check the expiration date, the video may skip to a portion of the video that shows the user how to check the expiration date of the fire extinguisher.

The task apparatus 104 may create templates by receiving information that defines one or more form fields of the compliance template based on the compliance task. The information is derived from a compliance policy, manual, workbook, or the like. The task apparatus 104, in further embodiments, includes one or more interactive multimedia elements in the compliance template that are associated with at least one of the one or more form fields. The task apparatus 104, in some embodiments, electronically presents the compliance template during the compliance task to gather compliance information related to the compliance task. Example use cases include compliance task management for hospitals, nursing homes, assisted living centers, blood labs, and related healthcare facilities.

The task apparatus 104, in one embodiment, is part of a multi-purpose system, e.g., task management system 100 that organizes, manages, and connects various touch points across an entire organization and its channels offline and online. In certain embodiments, the task apparatus 104 automates, integrates, connects numerous engagements, interactions, communications, stories, conversations, tasks, etc., and connects with numerous other systems to fulfill the needs of the organization, company, business, etc. on any electronic device to increase efficiency, effectiveness, security, compliance, safety, presentation, etc., among all stakeholders in an ecosystem/network etc.

As described herein, the task management system 100 may be embodied as a remote, data-driven hospital safety and compliance system whose policies, activities, reports, and timelines are governed by the joint commission—and may be used to integrate with other governing bodies and agencies including but not limited to the occupational safety and health administration ("OSHA").

In certain embodiments, to generate the compliance template, an online manual is accessed, e.g., from a local repository, from a cloud storage site such as Dropbox®, or the like. A master template may be created that follows the layout of the manual and matches setup, checklist, sub-templates, etc., so a user, hospital, employee, or third-party vendor who has to do certain tasks can track them in sequence. The data may then be filtered and queried to get the desired data. Also, any information or content that is uploaded into the task management system 100 is time and date stamped so that a history can be developed that includes most, if not all, interactions with the task management system 100. Maintaining a time-stamped access history is important because if the joint commission inspects the hospital, for example, it can track the history of compliance or noncompliance for that respective year.

As described above, a series of templates can be created to assist in ensuring compliance with various regulations from the compliance manual for an organization, e.g., a hospital. In one example embodiment, hospital employees and outside vendors answer questions, provide responses to survey questions, make comments where necessary related to whether an item such as a physical item needs to be repaired, etc. The data is then captured and used to generate reports, trends, etc. Reminders can be sent based upon a timeline of how long the organization has until one or more of its compliance items is out of compliance. The reminders may be sent via email, text message, chat message, push notification, and/or the like.

In certain embodiments, the task apparatus 104 is embodied as a mobile program, application, or the like that can be a web application, for instance, and is downloadable. In such an embodiment, the mobile application may be optimized for integration with third-party systems and includes an interactive image of the hospital floor plan that includes blueprints for sprinkler systems, exit signs, exit doors, etc. that are highlighted using hotspots that present questions, surveys, forms, reports, data, etc. when the hotspots are interacted with on the map. The map may be included on a compliance template so that the user can locate and gain more information on the location of the compliance task, equipment at the location, and/or the like. Furthermore, as the user walks the physical layout of the hospital, the user can capture pictures of any defective sprinklers, exit signs, exit doors, etc., and then update the interactive image/map of the floor plan so that up-to-date information is available prior to a user going out to inspect the hospital floor with a physical inspection.

In one embodiment, the task apparatus 104 provides a solution over conventional compliance systems in that it has universal applicability for different organizations or divisions within an organization based on generating different compliance templates. Furthermore, the task apparatus 104 improves the security of the compliance system by enforcing permissions, access control lists, time-stamping access and changes, and/or the like. Moreover, the task apparatus 104 integrates with various third-party applications such as cloud storage providers, e.g., Dropbox®, advertisers, affiliates, artificial intelligence engines, predictive analytics engines, and/or the like. The task apparatus 104 also provides and sends compliance reminders automatically, generates and maintains inspection schedules, and/or the like. The foregoing improvements remove many of manual steps previously done on paper and reduces errors in compliance maintenance, which can be crucial to avoid missing compliance deadlines, creating errors in the compliance paperwork, and/or the like.

In various embodiments, the task apparatus 104 may be embodied as a hardware appliance that can be installed or deployed on an information handling device 102, on a server 108, or elsewhere on the data network 106. In certain embodiments, the task apparatus 104 may include a hardware device such as a secure hardware dongle or other hardware appliance device (e.g., a set-top box, a network appliance, or the like) that attaches to a device such as a laptop computer, a server 108, a tablet computer, a smart phone, a security system, or the like, either by a wired connection (e.g., a universal serial bus ("USB") connection) or a wireless connection (e.g., Bluetooth®, Wi-Fi, near-field communication ("NFC"), or the like); that attaches to an electronic display device (e.g., a television or monitor using an HDMI port, a DisplayPort port, a Mini DisplayPort port, VGA port, DVI port, or the like); and/or the like. A hardware appliance of the task apparatus 104 may include a power interface, a wired and/or wireless network interface, a graphical interface that attaches to a display, and/or a semiconductor integrated circuit device as described below, configured to perform the functions described herein with regard to the task apparatus 104.

The task apparatus 104, in such an embodiment, may include a semiconductor integrated circuit device (e.g., one or more chips, die, or other discrete logic hardware), or the like, such as a field-programmable gate array ("FPGA") or other programmable logic, firmware for an FPGA or other programmable logic, microcode for execution on a microcontroller, an application-specific integrated circuit ("ASIC"), a processor, a processor core, or the like. In one embodiment, the task apparatus 104 may be mounted on a printed circuit board with one or more electrical lines or connections (e.g., to volatile memory, a non-volatile storage medium, a network interface, a peripheral device, a graphical/display interface, or the like). The hardware appliance may include one or more pins, pads, or other electrical connections configured to send and receive data (e.g., in communication with one or more electrical lines of a printed circuit board or the like), and one or more hardware circuits and/or other electrical circuits configured to perform various functions of the task apparatus 104.

The semiconductor integrated circuit device or other hardware appliance of the task apparatus 104, in certain embodiments, includes and/or is communicatively coupled to one or more volatile memory media, which may include but is not limited to random access memory ("RAM"), dynamic RAM ("DRAM"), cache, or the like. In one embodiment, the semiconductor integrated circuit device or other hardware appliance of the task apparatus 104 includes and/or is communicatively coupled to one or more non-volatile memory media, which may include but is not limited to: NAND flash memory, NOR flash memory, nano random access memory (nano RAM or NRAM), nanocrystal wire-based memory, silicon-oxide based sub-10 nanometer process memory, graphene memory, Silicon-Oxide-Nitride-Oxide-Silicon ("SONOS"), resistive RAM ("RRAM"), programmable metallization cell ("PMC"), conductive-bridging RAM ("CBRAM"), magneto-resistive RAM ("MRAM"), dynamic RAM ("DRAM"), phase change RAM ("PRAM" or "PCM"), magnetic storage media (e.g., hard disk, tape), optical storage media, or the like.

The data network 106, in one embodiment, includes a digital communication network that transmits digital communications. The data network 106 may include a wireless network, such as a wireless cellular network, a local wireless network, such as a Wi-Fi network, a Bluetooth® network, a near-field communication ("NFC") network, an ad hoc network, and/or the like. The data network 106 may include a wide area network ("WAN"), a storage area network ("SAN"), a local area network (LAN), an optical fiber network, the internet, or other digital communication network. The data network 106 may include two or more networks. The data network 106 may include one or more servers, routers, switches, and/or other networking equipment. The data network 106 may also include one or more computer readable storage media, such as a hard disk drive, an optical drive, non-volatile memory, RAM, or the like.

The wireless connection may be a mobile telephone network. The wireless connection may also employ a Wi-Fi network based on any one of the Institute of Electrical and Electronics Engineers ("IEEE") 802.11 standards. Alternatively, the wireless connection may be a Bluetooth® connection. In addition, the wireless connection may employ a Radio Frequency Identification ("RFID") communication including RFID standards established by the International Organization for Standardization ("ISO"), the International Electrotechnical Commission ("IEC"), the American Society for Testing and Materials® (ASTM®), the DASH7™ Alliance, and EPC Global™.

Alternatively, the wireless connection may employ a ZigBee® connection based on the IEEE 802 standard. In one embodiment, the wireless connection employs a Z-Wave® connection as designed by Sigma Designs®. Alternatively, the wireless connection may employ an ANT® and/or ANT+® connection as defined by Dynastream® Innovations Inc. of Cochrane, Canada.

The wireless connection may be an infrared connection including connections conforming at least to the Infrared Physical Layer Specification ("IrPHY") as defined by the Infrared Data Association® ("IrDA"®). Alternatively, the wireless connection may be a cellular telephone network communication. All standards and/or connection types include the latest version and revision of the standard and/or connection type as of the filing date of this application.

The one or more servers 108, in one embodiment, may be embodied as blade servers, mainframe servers, tower servers, rack servers, and/or the like. The one or more servers 108 may be configured as mail servers, web servers, application servers, FTP servers, media servers, data servers, web servers, file servers, virtual servers, and/or the like. The one or more servers 108 may be communicatively coupled (e.g., networked) over a data network 106 to one or more information handling devices 102. The one or more servers 108 may store data associated with an information handling device 102.

Figure 2:
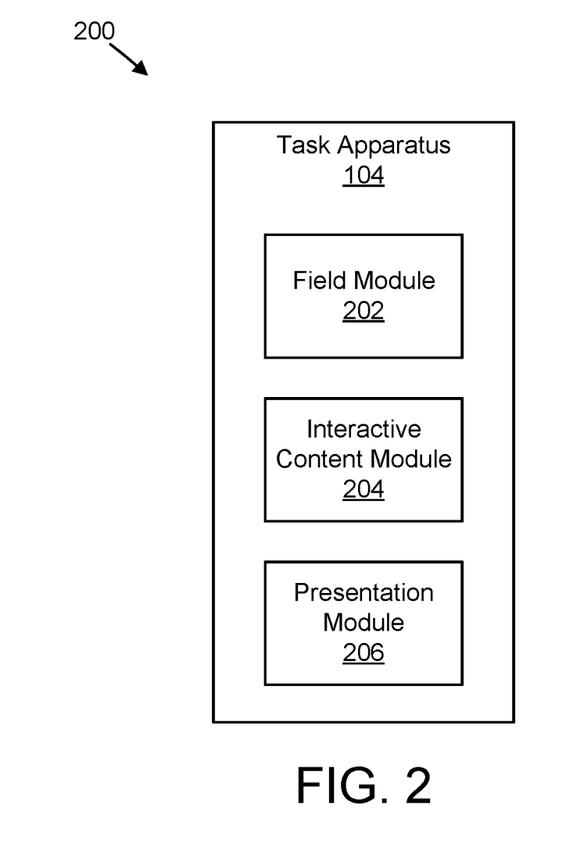
FIG. 2 is a schematic block diagram illustrating one embodiment of an apparatus for task management.

FIG. 2 illustrates one embodiment of an apparatus 200 for a task management system. The apparatus 200, in certain embodiments, includes an instance of a task apparatus 104. The task apparatus 104, in one embodiment, includes one or more of a field module 202, an interactive content module 204, and a presentation module 206, which are described in more detail below.

The field module 202, in one embodiment, is configured to receive information for defining one or more form fields of a compliance template associated with a compliance task. As used herein, a compliance template is a template or form that presents questions for a user to fill in (in form fields) as the user performs a compliance task. Further, as used herein, a form field may be an electronic or digital field for collecting information that is entered by a user. Examples of form fields may include text boxes, radio buttons, drop down lists, spin controls, and/or the like. The user may provide input or enter information in the form fields that can be collected when the form is submitted.

The compliance template may comprise one or more form fields that are based on a compliance policy, manual, rules, regulations, and/or the like. The compliance policy may be established by an accreditation board or organization, by a government or other regulatory agency, and/or the like. For example, hospitals may be required to comply with policies and regulations established by The Joint Commission in order to earn and maintain their accreditation as a healthcare provider. The field module 202 may access the policy from a local repository, a website, a file sharing site (e.g., Dropbox®), and/or the like.

In one embodiment, the field module 202 periodically checks for updates to the policy, checks for new versions of the policy, receives a notification that a new version of the policy is available, checks change logs for changes to the policy, and/or the like such that the field information in the compliance template can be updated, modified, removed, added to, or the like. In this manner, the compliance templates can be kept up to date without requiring the user to go through and manually change each of the templates.

A compliance task, as used herein, refers to a task, job, duty, workflow, or the like that needs to be performed and reported to comply with the compliance requirements of the compliance policy. For instance, in a healthcare scenario, a compliance task may be to check the status of various equipment (e.g., whether the equipment is in good working order, needs repairs, or is obsolete or broken), determine whether certain processes are being implemented according to the regulated guidelines (e.g., that the steps are being performed in the correct or suggested order), check the status of doctors, nurses, and other hospital personnel (e.g., ensuring licenses, certifications, etc. are valid and up to date), and/or the like. Thus, a compliance task may be associated with a piece of equipment, a process, a person, a location, and/or the like.

In one embodiment where the compliance task is associated with a piece of equipment, the equipment may be identified using an identification tag (e.g., an RFID tag, a barcode, a QR code, a wireless signal (e.g., a Bluetooth® signal), an IP or MAC address, and/or the like) that is located on the equipment. In such an embodiment, a location service may be used to determine the location of the equipment within a building, on a floor, etc., and display the equipment's location on a map that is included in the compliance template.

In one embodiment, the field module 202 parses the compliance policy, using natural language processing, regular expressions, and/or other text processing methods, to identify different compliance tasks and requirements for completing the compliance tasks, and generates form fields for gathering or collecting information for the compliance task. For instance, the field module 202 may identify that a compliance task that requires the user to enter an expiration date, a supervisor name, and a date that the last compliance task was completed. The field module 202 may identify these requirements (e.g., if formatted as a question in the compliance policy) and may generate labels and fields for gathering this information in a web form or other electronic form.

In certain embodiments, in addition to the compliance requirements from the compliance policy/manual, the field module 202 may receive information for form fields based on compliance tasks that an administrator or other user has created, e.g., custom or special compliance tasks that may not be listed in the compliance policy/manual.

The interactive content module 204, in one embodiment, is configured to include one or more interactive multimedia elements in the compliance template. The interactive multimedia elements may include interactive videos, images, slideshows, quizzes, surveys, polls, hotspots, and/or other interactive content. An interactive video, for example, may include video branching where a segment of the video is played based on the user's response to a question on the video (as described in more detail in U.S. Pat. No. 9,535, 577, which is incorporated by reference herein in its entirety).

In certain embodiments, the interactive content module 204 accesses the interactive content from a local repository, from a remote server, from a content hosting site (e.g., YouTube®), from a social media platform (e.g., Facebook®), and/or the like. The interactive content may be tagged with keywords that make it searchable so that the interactive content module 204 can locate interactive content that is relevant to the compliance task. For example, if the compliance task is related to x-ray equipment, the interactive content module 204 may filter the available interactive content based on the keyword or tag "x-ray" to find interactive content that is related to the compliance task. The interactive content module 204 may further refine or narrow the search using additional, secondary keywords (e.g., "MRI x-rays).

The interactive content module 204, therefore, may integrate, overlay, inlay, or otherwise place interactive content that is associated with the compliance task within the compliance template. For instance, the interactive content element may include instructional videos on how to perform a compliance check for the compliance task, a live-streaming video to/from an administrator or third-party vendor that walks a user through performing a compliance task in real time, a webinar, a training video, a slideshow with steps for performing the compliance check (which may also include video/images), and/or the like.

In one embodiment, the presentation module 206 is configured to electronically or digitally present the compliance template during a compliance task to gather compliance information for the compliance task. The presentation module 206, for instance, may present the compliance template in a web browser, in a mobile application, and/or the like on a display of a user's device such as a smart phone, a tablet device, a smart watch, an head-mounted display unit, a virtual or augmented reality device, and/or the like.

In one embodiment, the presentation module 206 tracks various characteristics/analytics/metrics of the user's interaction with the compliance template. For instance, the presentation module 206 may track how long a compliance template is open, how long a user views an interactive content element, which interactive content elements the user interacts with, how long it takes a certain user to complete a compliance task, and/or the like. These metrics may be used to determine how efficient certain users are, how difficult certain compliance tasks are, which vendors are the most efficient/cost effective, where more training needs to be implemented and for which users, and/or the like.

In this manner, the user performing the compliance check will have access to the compliance templates/forms that are available to the user as the user performs compliance tasks/checks within their organization, e.g., within a hospital. Initially, the user may need to provide credentials (e.g., username/password, biometric information, etc.) to verify the user's identity to access the compliance template. The user can then perform the compliance task on site, using their electronic device, and enter compliance information into the form fields, take images of the compliance check to verify the user's responses (e.g., images of equipment), live stream the compliance check (e.g., for verification, feedback, training, or the like), and/or the like.

In certain embodiments, the compliance templates and tasks are searchable using tags, keywords, or the like so that administrators or other users can locate, find, and review compliance templates, compliance tasks, and/or check the status of the compliance templates/tasks. The user may further search and filter the compliance templates by building, user, compliance task, equipment, and/or any combination of the foregoing. The user may further filter the compliance tasks by tasks that are overdue, tasks that need to be done now, tasks that need to be done in the next week, month, year, etc., and/or the like so that the user can get a snapshot of the compliance status of the organization. A daily/weekly/monthly summary report may further be created to give an administrator, supervisor, manager, or the like a daily status of their compliance tasks.

Figure 3:
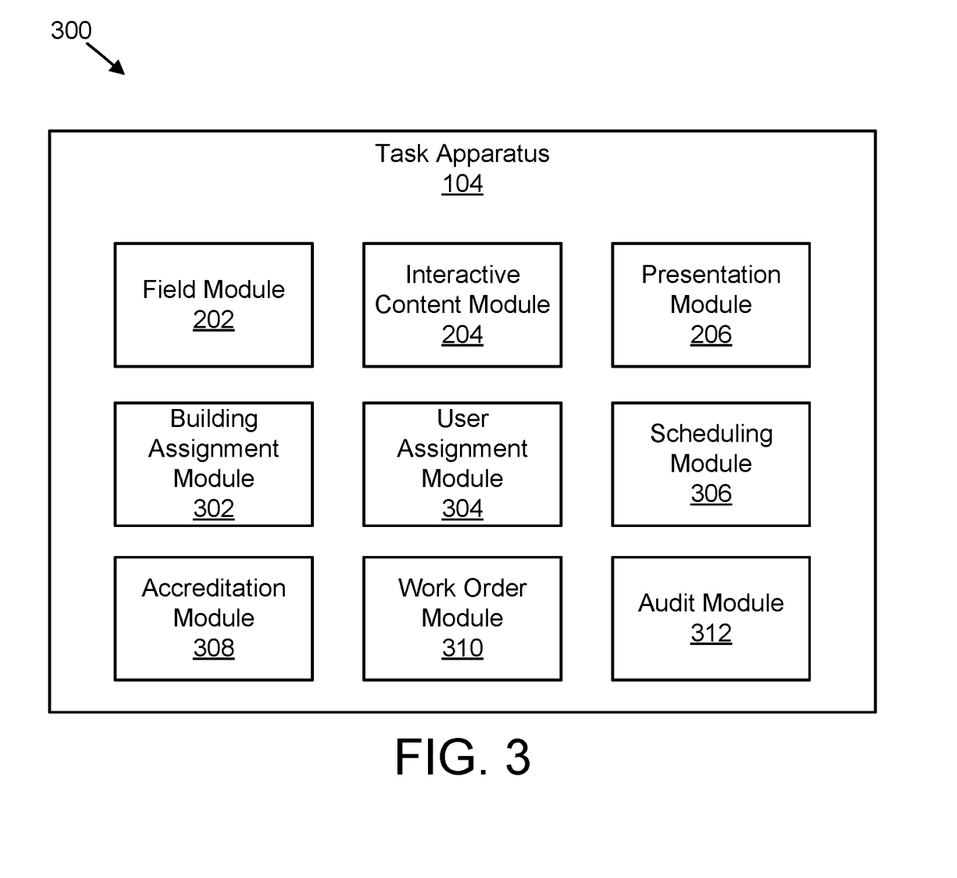
FIG. 3 is a schematic block diagram illustrating one embodiment of another apparatus for task management.

FIG. 3 illustrates one embodiment of an apparatus 300 for a task management system. The apparatus 300, in certain embodiments, includes an instance of a task apparatus 104. The task apparatus 104, in one embodiment, includes one or more of a field module 202, an interactive content module 204, and a presentation module 206, which may be substantially similar to the field module 202, the interactive content module 204, and the presentation module 206 described above with reference to FIG. 2. Furthermore, in certain embodiments, the task module 104 includes one or more of a building assignment module 302, a user assignment module 304, a scheduling module 306, an accreditation module 308, a work order module 310, and an audit module 312, which are described in more detail below.

In one embodiment, the building assignment module 302 is configured to assign the compliance template to a building, wing, floor, center, room, or the like of an organization. For example, the compliance template may be assigned to the building where the emergency room is located, to the floor of the hospital where the trauma center is located, and/or the like. In such an embodiment, the organization, e.g., the hospital, may maintain a master template that includes each of the sub-templates for each building or other part of the physical structure or layout of the organization. Thus, the template may be one of a plurality of templates that are assigned to the building and associated with different compliance tasks for the building.

In certain embodiments, the user assignment module 304 is configured to assign one or more users to the compliance task associated with the compliance template such that the one or more users are the only users allowed to enter compliance information into the compliance template during the compliance task. For example, the user assignment module 304 may assign certain hospital staff members, maintenance crew, or the like to different compliance tasks based on the user's experiences, education, and/or the like, or in response to user input, e.g., from a hospital administrator.

The user assignment module 304 may assign third-party vendors such as contract workers, technicians, equipment repair and maintenance personnel, or the like to compliance tasks so that approved third-party vendors can enter compliance information into the compliance template for a compliance task. For example, if a hospital hires a third-party service to provide, maintain, and repair fire extinguishers, these users may be added to the list of approved third-party vendors who can perform compliance tasks for the fire extinguishers because they have the expertise and experience to verify that the fire extinguishers comply with the compliance requirements of the compliance task as defined by the policy. The user assignment module 304, therefore, defines permissions, access control lists, and/or the like for the compliance tasks and the associated compliance templates.

In one embodiment, the scheduling module 306 is configured to determine deadlines for completing each of the compliance tasks, as defined by the compliance policy. For example, the compliance policy may require that fire alarms within the hospital be tested every three months. Based on the deadlines for each compliance task, the scheduling module 306 generates a compliance schedule for each compliance task and associated the compliance schedule with each compliance template for each compliance task.

The scheduling module 306 may be graphically displayed as a timeline, a calendar, and/or the like that includes reminders and deadlines for the compliance tasks that need to be completed, or that have already been completed. Furthermore, the scheduling module 306 may include a color scheme for different deadlines for the compliance tasks. For example, if a compliance task is complete it may show up as green, if a compliance task is late (past the deadline) it may show up as red, reminders may show up as yellow, orange, or the like based on the time between the reminder and the scheduled deadline date, and/or the like. In this manner, a user can quickly see the complete schedule for completion of a compliance task.

Furthermore, the scheduling module 306 may generate and send one or more reminders, push notifications, alerts, emails, text messages, chat messages, and/or the like for completing the compliance tasks. The scheduling module 306 may set different points in time for sending reminders, such as one week before the deadline, two weeks before the deadline, one month before the deadline, three months before the deadline, semi-annually, annually, and/or the like, and/or any combination of the foregoing.

For example, continuing with the fire alarm example, if the scheduling module 306 determines that the fire alarms need to be tested every three months, the scheduling module 306 may send reminders to users who are assigned to the compliance task two months before the deadline, one month before the deadline, two weeks before the deadline, a week before the deadline, three days before the deadline, and the day before the deadline, and/or the like. In this manner, the scheduling module 306 can send constant reminders about completing compliance tasks at various points in time leading up to the compliance deadline.

In one embodiment, the accreditation module 308 is configured to send the results of the compliance task, e.g., the information that was entered into the compliance template to an accreditation organization, and/or batch a plurality of completed compliance templates to be sent to the accreditation organization as evidence that the organization is in compliance with the policies, rules, regulations, or the like that the accreditation organization established. The accreditation module 308 may have a direct connection (online) to the accreditation organization so that when a compliance template is complete, the accreditation module 308 sends the template directly to the accreditation organization. In certain embodiments, an administrator, manager, supervisor, or the like may have to sign off on the completed compliance template prior to the accreditation module 308 sending it to the accreditation organization.

In one embodiment, the work order module 310 is configured to generate one or more work orders, requests for proposals, or the like for third-party vendors based on the compliance task and the schedule for completing the compliance task. As used herein, a work order may be a request to complete a task or job as it relates to the compliance task and may be generated for maintenance services, inspection services, equipment management services, and/or the like. For instance, if the elevators in a hospital need to be serviced, the work order module 310 may generate and send a work order request to an elevator service company that the hospital has approved as a third-party vendor for the hospital. The work order module 310 may check the deadline for completing the compliance check and send the work order some time prior to the deadline so that the third-party vendor has time to schedule and prepare to work on the compliance task.

In one embodiment, the audit module 312 is configured to maintain a user login history, a history of users that entered information into the compliance template, timestamps for each access and data entry into the compliance templates, and/or the like. In this manner, the audit module 312 can provide a snapshot or history of which users accessed the templates, when they were last modified, when new templates were created, which users entered data into the templates, when templates were completed and/or submitted for review/accreditation, and/or the like. In some embodiments, the audit module 312 may verify or authenticate and protect completed compliance templates using a digital signature, a blockchain system, encryption, and/or the like (e.g., prior to sending the completed template to an accreditation organization).

Figure 4:
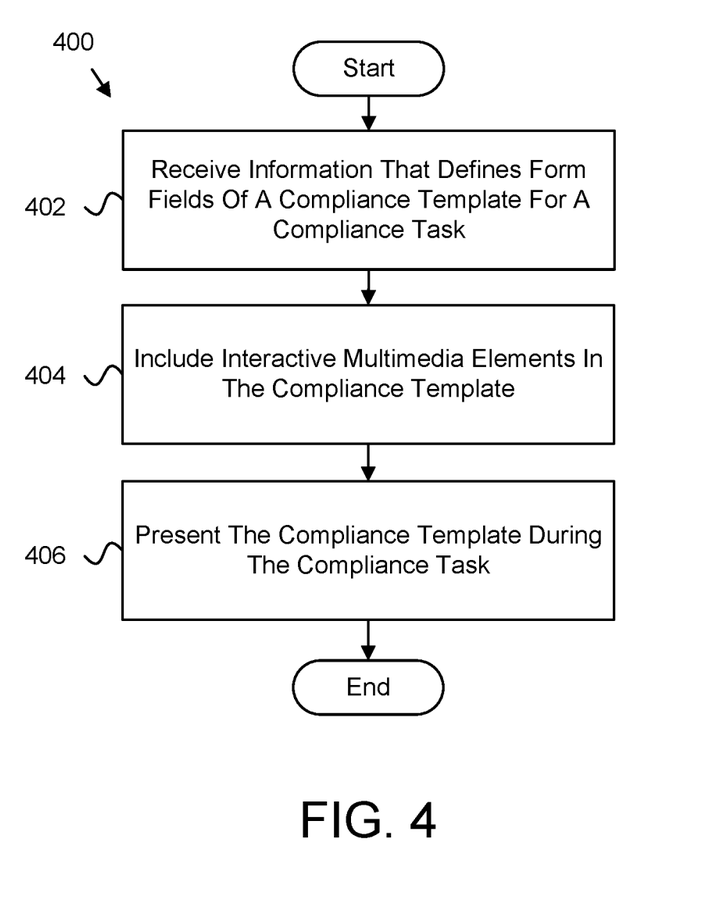
FIG. 4 is a schematic flow-chart diagram illustrating one embodiment of a method for task management.

FIG. 4 illustrates a schematic flow-chart diagram of one embodiment of a method 400 for a task management system. In one embodiment, the method 400 begins and receives 402 information for defining one or more form fields of a compliance template associated with a compliance task. The information may be derived from a compliance policy. In further embodiments, the method 400 includes 404 one or more interactive multimedia elements in the compliance template. The one or more interactive multimedia elements may be associated with at least one of the one or more form fields. In some embodiments, the method 400 electronically presents 406 the compliance template during the compliance task to gather compliance information related to the compliance task, and the method 400 ends. In certain embodiments, the field module 202, the interactive content module 204, and/or the presentation module 206 perform the various steps of the method 400.

Figure 5:
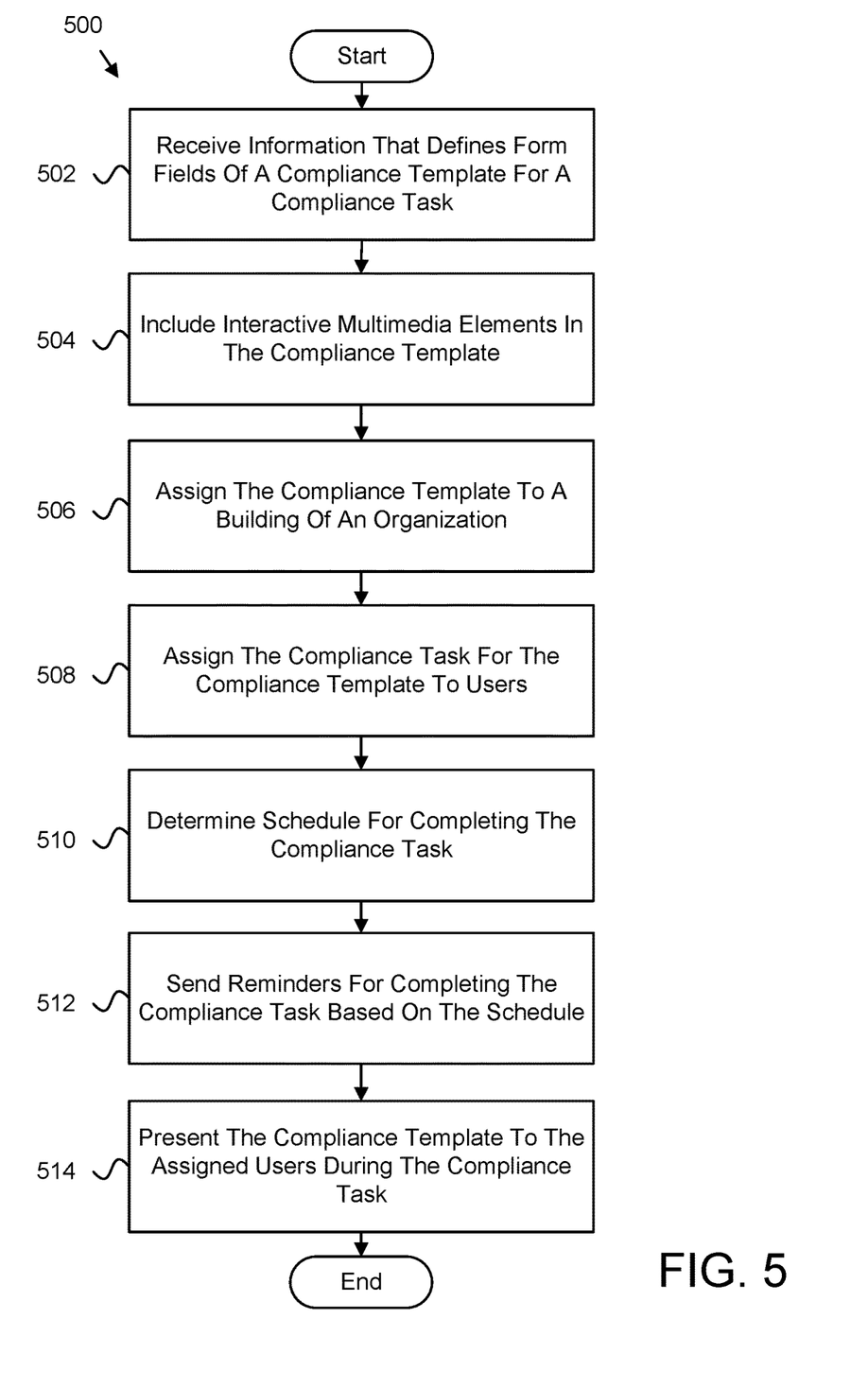
FIG. 5 is a schematic flow-chart diagram illustrating one embodiment of another method for task management.

FIG. 5 illustrates a schematic flow-chart diagram of one embodiment of a method 500 for a task management system. In one embodiment, the method 500 begins and receives 502 information for defining one or more form fields of a compliance template associated with a compliance task. The information may be derived from a compliance policy. In further embodiments, the method 500 includes 504 one or more interactive multimedia elements in the compliance template. The one or more interactive multimedia elements may be associated with at least one of the one or more form fields.

In some embodiments, the method 500 assigns 506 the compliance template to a building (or a section, wing, floor, room, or the like) of an organization. In further embodiments, the method 500 assigns 508 the compliance task associated with the compliance template to one or more users such that the one or more users are the only users who are authorized to enter information into the compliance template and submit the completed compliance template.

In some embodiments, the method 500 determines 510 a schedule for completing the compliance task based on a compliance deadline for the compliance task and sends 512 reminders for completing the compliance task at points in time prior to the deadline based on the determined schedule. In certain embodiments, the method 500 electronically presents 514 the compliance template during the compliance task to gather compliance information related to the compliance task, and the method 500 ends. In certain embodiments, the field module 202, the interactive content module 204, the presentation module 206, the building assignment module 302, the user assignment module 304, and/or the scheduling module 306 perform the various steps of the method 500.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An apparatus, comprising:
a processor;
a memory that stores code executable by the processor to:
parse a compliance policy using natural language processing to identify different compliance tasks and requirements for completing a compliance task;
determine information for defining one or more form fields for a digital compliance template associated with the compliance task based on the identified requirements for the compliance tasks, the one or more form fields comprising digital fields for receiving user input that are dynamically determined and integrated into the compliance template, the compliance template comprising a deadline for completing the compliance task associated with the compliance template;
generate one or more reminders for completing the compliance task at predefined points in time prior to the deadline;
dynamically generate the one or more form fields of the compliance template associated with the compliance task based on the generated information derived from the compliance policy;
identify one or more interactive multimedia elements related to the compliance task using one or more keywords determined based on the identified requirements for the compliance tasks;
integrate the identified one or more interactive multimedia elements in the compliance template associated with the compliance task; and
electronically present the compliance template during the compliance task to gather compliance information related to the compliance task.

2. The apparatus of claim 1, wherein the code is further executable by the processor to assign the compliance template to a building of an organization, the template comprising one of a plurality of templates assigned to the building and associated with different compliance tasks for the building.

3. The apparatus of claim 1, wherein the one or more interactive multimedia elements is selected from the group consisting of a survey, a quiz, an instructional video, a training video, a webinar, and a how-to slideshow.

4. The apparatus of claim 1, wherein the code is further executable by the processor to assign one or more users to the compliance task associated with the compliance template such that the one or more users are the only users allowed to enter compliance information into the compliance template to complete the compliance task.

5. The apparatus of claim 1, wherein the code is further executable by the processor to provide the compliance information that is entered into the compliance template to an accreditation service as evidence of an organization's compliance with the compliance policy.

6. The apparatus of claim 1, wherein the deadline is defined by the compliance policy.

7. The apparatus of claim 6, wherein the code is further executable by the processor to generate a compliance schedule for the compliance task based on the deadline for completing the compliance task.

8. The apparatus of claim 1, wherein the code is further executable by the processor to send the one or more reminders to one or more users who are assigned to the compliance task at the predefined points in time prior to the deadline in response to the compliance task not being completed.

9. The apparatus of claim 1, wherein the code is further configured to generate one or more work orders for one or more third-party vendors based on the compliance task and a schedule for completion of the compliance task.

10. The apparatus of claim 1, wherein the one or more work orders are for third-party services selected from the group comprising maintenance services, inspection services, and equipment management services.

11. The apparatus of claim 1, wherein the compliance task is associated with one or more pieces of equipment, the one or more pieces of equipment identified using an identification tag located on the one or more pieces of equipment and a location service that is configured to determine the location of the one or more pieces of equipment based on the identification tag.

12. The apparatus of claim 1, wherein the compliance policy and the compliance task are associated with a healthcare organization.

13. A method, comprising:
parsing a compliance policy using natural language processing to identify different compliance tasks and requirements for completing a compliance task;
determining information for defining one or more form fields for a digital compliance template associated with the compliance task based on the identified requirements for the compliance tasks, the one or more form fields comprising digital fields for receiving user input that are dynamic ally determined and integrated into the compliance template, the compliance template comprising a deadline for completing the compliance task associated with the compliance template;

generating one or more reminders for completing the compliance task at predefined points in time prior to the deadline;

dynamically generating the one or more form fields of the compliance template associated with the compliance task based on the generated information derived from the compliance policy;

identifying one or more interactive multimedia elements related to the compliance task using one or more keywords determined based on the identified requirements for the compliance tasks;

integrating the identified one or more interactive multimedia elements in the compliance template associated with the compliance task; and electronically presenting the compliance template during the compliance task to gather compliance information related to the compliance task.

14. The method of claim 13, further comprising assigning the compliance template to a building of an organization, the template comprising one of a plurality of templates assigned to the building and associated with different compliance tasks for the building.

15. The method of claim 13, further comprising assigning one or more users to the compliance task associated with the compliance template such that the one or more users are the only users allowed to enter compliance information into the compliance template to complete the compliance task.

16. The method of claim 13, wherein the deadline is defined by the compliance policy.

17. The method of claim 16, further comprising generating a compliance schedule for the compliance task based on the deadline for completing the compliance task.

18. A program product comprising a computer readable storage medium that stores code executable by a processor, the executable code comprising code to perform:

parsing a compliance policy using natural language processing to identify different compliance tasks and requirements for completing a compliance task;

determining information for defining one or more form fields for a digital compliance template associated with the compliance task based on the identified requirements for the compliance tasks, the one or more form fields comprising digital fields for receiving user input that are dynamic ally determined and integrated into the compliance template, the compliance template comprising a deadline for completing the compliance task associated with the compliance template;

generating one or more reminders for completing the compliance task at predefined points in time prior to the deadline;

dynamically generating the one or more form fields of the compliance template associated with the compliance task based on the generated information derived from the compliance policy;

identifying one or more interactive multimedia elements related to the compliance task using one or more keywords determined based on the identified requirements for the compliance tasks;

integrating the identified one or more interactive multimedia elements in the compliance template associated with the compliance task; and electronically presenting the compliance template during the compliance task to gather compliance information related to the compliance task.

19. The method of claim 13, further comprising sending the one or more reminders to one or more users who are assigned to the compliance task at the predefined points in time prior to the deadline in response to the compliance task not being completed.

20. The program product of claim 18, wherein the executable code comprises code to perform sending the one or more reminders to one or more users who are assigned to the compliance task at the predefined points in time prior to the deadline in response to the compliance task not being completed.

\* \* \* \* \*